US009267102B2

(12) United States Patent
Osterloh

(10) Patent No.: US 9,267,102 B2
(45) Date of Patent: Feb. 23, 2016

(54) ALGAE POND CIRCULATION

(71) Applicant: James D. Osterloh, West Richland, WA (US)

(72) Inventor: James D. Osterloh, West Richland, WA (US)

(*) Notice: Subject to any disclaimer, the term of this patent is extended or adjusted under 35 U.S.C. 154(b) by 47 days.

(21) Appl. No.: 13/842,338

(22) Filed: Mar. 15, 2013

(65) Prior Publication Data

US 2014/0273170 A1    Sep. 18, 2014

(51) Int. Cl.
*C12M 1/04* (2006.01)
*C12M 1/00* (2006.01)
*C12M 1/02* (2006.01)

(52) U.S. Cl.
CPC .............. *C12M 27/04* (2013.01); *C12M 21/02* (2013.01); *C12M 27/00* (2013.01)

(58) Field of Classification Search
CPC ....... C12M 21/02; C12M 27/04; C12M 27/00
USPC .......................................... 435/292.1; 47/1.4
See application file for complete search history.

(56) References Cited

U.S. PATENT DOCUMENTS

| 3,913,156 | A  | * | 10/1975 | Howorth ........................ 5/689 |
| 4,170,898 | A  | * | 10/1979 | Salter ............................ 73/148 |
| 6,659,689 | B1 | * | 12/2003 | Courtney et al. ............. 405/186 |
| 2004/0062140 | A1 | * | 4/2004 | Cadogan et al. .............. 366/144 |
| 2008/0009055 | A1 | * | 1/2008 | Lewnard ....................... 435/262 |
| 2010/0281836 | A1 | * | 11/2010 | Vanhoutte et al. ............... 56/9 |

* cited by examiner

*Primary Examiner* — Nathan Bowers
*Assistant Examiner* — Gautam Prakash
(74) *Attorney, Agent, or Firm* — John Chandler

(57) ABSTRACT

Systems, apparatuses and methods for circulating and agitating algae ponds or reservoirs are described. Inflatable or floatable masses resident in the algae ponds are cyclically or rhythmically moved thereby causing propagating waves to advance along ponds. Waves encourage increased equilibrium of oxygen and carbon dioxide between ambient air and growth medium and thereby improved growth of algae and increased production of biomass. With relatively little energy input, large quantities of algae or biomass may be grown in relatively large ponds and on an economically viable commercial scale.

15 Claims, 6 Drawing Sheets

ALGAE POND CIRCULATION

FIELD

The present invention is related to functions related to circulation of algae or biomass in cultivation ponds or reservoirs. More specifically, the invention relates to propagating waves efficiently across relatively large ponds and reservoirs to promote oxygen delivery to and growth of biomass.

BACKGROUND

A massive quantity of carbon is available in the atmosphere in the form of carbon dioxide. Within the past 150 years, the concentration of carbon dioxide in the atmosphere has increased substantially. Whatever the cause, atmospheric carbon dioxide could be an economical, industrially viable and successful source of fuel, food, building materials and the like if combined with other constituents. One way of processing atmospheric carbon dioxide is to capture it through photosynthesis. Algae is one medium through which photosynthesis can be put to use.

Algae has many advantages over other plants. Plants as used herein include organisms capable of performing or facilitating photosynthesis. Advantages of algae include fast growth, high sequestration of solar energy, ease of processing and good nutrition. Over the last two decades, algae has become a popular focus of research for engineers and scientists. Various aspects of algae have been studied. For instance, algae can be used as a food substitute, a medium for carbon sequestration, an agent for generating oils and converting the oils into biodiesels for use as an energy source.

Therefore, it is important for scholars, researchers and producers to quickly cultivate massive quantities of algae to serve as a raw material for further processing. Algae cultivation is often the bottleneck for producing products on a viable or economic scale. Algae cultivation requires sufficient light, carbon dioxide and nutrients. Sunlight and carbon dioxide are in abundance. However, efficient and effective delivery of light, carbon dioxide and nutrients to a substantial quantity of growing algae cells is tricky.

One popular and relatively inexpensive location for cultivating algae is in ponds or reservoirs. Ponds and reservoirs can be of any size; large ponds could be a source of large quantities of algae. However, to effectively use light energy in a pond cultivation process, light must reach the cells of the algae. Cultivation ponds suffer from several drawbacks. As algae grows at the surface of cultivation ponds, newly formed algae creates a barrier to and throws a shadow on other algae found slightly lower in the medium. Carbon dioxide is captured by the top layers of the algae and a decreasing concentration of carbon dioxide is available for algae growing deeper in the medium.

Over the years, many systems and devices have been proposed to overcome these and other limitations associated with algae ponds. For example, transparent tubes and open-air circulation troughs have been proposed to more efficiently expose algae to light. Other solutions have suggested the use of jets, paddle wheels, etc. to circulate the growth medium (e.g., water) or to circulate the algae in container (e.g., ponds, troughs, tubes). However, nearly all of these inventions are prohibitively expensive or are incapable of producing relatively large quantities of algae. One problem with these systems is that jets and other components are too vigorous for most forms of algae because algae is relatively fragile. Algae does not contain or require substantial amounts of cellulosic fibers that are necessary to support non-aqueous plants such as trees and land-based crops. Another problem associated with efficient circulation is that mechanical energy input into the system is quickly damped and circulation is thwarted. Pond photosynthesis reactors have been used at various stages in algae cultivation. Photosynthesis occurs near the surface of the reactors. Growth is initially fast, but growth rapidly declines over time. One reason is that sunlight fails to reach more than about one-half inch of the algae in the water in stagnate or circulated algae ponds. Further, algae tends to sink as it grows.

Canal style photosynthesis reactors have been proposed as an improvement over ponds. In a canal type photosynthesis reactor, the cultivation liquid is flowing, and a turbulent current produced between the fluid and the channel walls can provide effective mixing or agitation of the cultivation liquid (medium) and suspended algae cells. Thus, a cell growth curve of a general channel type photosynthesis reactor shows much better results for canal type photosynthesis reactors as compared to pools or ponds. However, both pond and canal style reactors suffer some disadvantages such as a propensity for contamination by other organisms, dust and other pollutants.

These and other disadvantages can be overcome with the teachings provided herein.

SUMMARY

Embodiments and techniques described herein include improved systems, apparatuses and methods for circulating and agitating algae ponds or reservoirs are described. Agitators create propagating waves which advance along some or all of the length of each pond. Propagating waves encourage increased equilibrium of oxygen and carbon dioxide between ambient air and growth medium and thereby improved growth of algae and increased production of biomass. Propagating waves circulate or cycle algae vertically through the water column thereby promoting healthy, sustainable algae growth. With relatively little energy input, large quantities of algae or biomass may be grown in relatively large ponds and on an economically viable commercial scale.

In certain implementations, relatively long and relatively narrow ponds are constructed and lined. Water and algae are introduced therein. An agitator includes a floatable or inflatable agitation element disposed in or adjacent to the water such as at or in a narrow end of each of the ponds. Each agitator may be operated independently of one another or may operate in tandem or synchronization with other agitators. The agitation elements are cyclically or rhythmically actuated or moved thereby creating propagating waves.

One or more compressors, ducts, dampers, bladders, vents and other elements are used to inflate the agitation elements. The various components of the system, including the agitation elements, and ponds may be sized according to various factors.

This Summary is provided to introduce a selection of concepts in a simplified form that are further described below in the Detailed Description. This Summary is not intended to identify key or essential features of the claimed subject matter, and this is not intended to be used to limit the scope of the claimed subject matter.

BRIEF DESCRIPTION OF THE DRAWINGS

While the appended claims set forth the features of the present invention with particularity, the invention, together with its objects and advantages, will be more readily appreciated from the following detailed description, taken in con

DETAILED DESCRIPTION

In the following description, for purposes of explanation, numerous specific details are set forth in order to provide an understanding of the invention. It will be apparent, however, to one skilled in the art that the invention can be practiced without these specific details. In other instances, structures, devices, systems and methods are shown only in block diagram form in order to avoid obscuring the invention.

Reference in this specification to "one embodiment" or "an embodiment" means that a particular feature, structure, or characteristic described in connection with the embodiment is included in at least one embodiment of the invention. Appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Broadly, embodiments and techniques of the present invention disclose or relate to systems and methods for circulating or agitating the medium, liquid, fluid or water in an algae cultivation pond. While there are various mechanisms to circulate or agitate the medium (e.g., impellers, propellers, water jets) a preferred mechanism is to periodically generate a propagating surface wave. In a preferred implementation, a propagating wave travels the length of the pond. It was found that a propagating wave adequately circulates the medium in the pond and does not appreciably disturb or inhibit growth of the algae. In fact, circulation of the medium by propagating waves was found to be preferable to other means of circulation.

Figure 1:
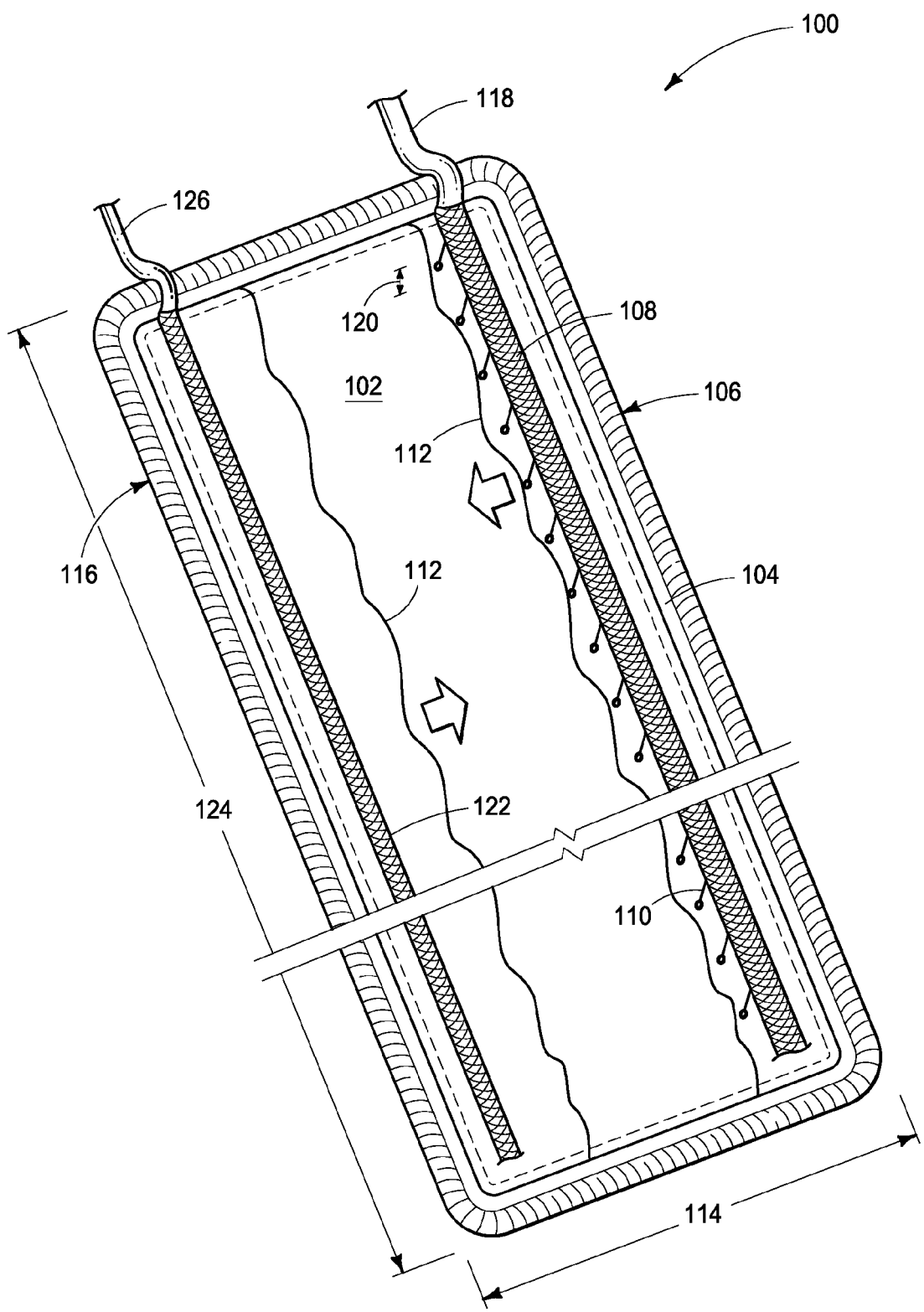
- FIG. 1 shows a perspective view of a single algae cultivation pond (herein "pond") according to one implementation of the invention.

FIG. 1 shows a perspective view of a single algae cultivation pond 100 (herein "pond") according to one implementation of the invention. With reference to FIG. 1, a pond 100 is at least partially filled with a cultivation medium (e.g., water, water-based solution of algae feeding nutrients) 102. The medium 102 is prevented from escaping the pond 100 by a liner 104 spread over the bottom and sides of the pond 100. The liner 104 also facilitates harvesting of the algae (not shown) as described in more detail below.

At or near a proximal side or edge 106 of the pond 100, an agitator 108 is installed or placed in the pond 100. The agitator may be maintained in place such as with permanent, temporary, moveable or removable anchors 110. The anchors 110 are optional. In one implementation, the agitator 108 is made of an inexpensive, flexible polyvinyl or plastic material. In this implementation, the agitator 108 is an inflatable bladder.

Intermittently, the agitator 108 is caused to generate a traveling or propagating wave 112 that travels the length or width 114 of the pond 100 to a distal side or edge 116 of the pond 100. In one implementation, the propagating wave 112 is created as follows. The agitator 108 is partially or fully submerged in the pond 100, and the agitator 108 is rapidly filled or pulsed with air through a hose or air duct 118. A fast-acting damper (not shown in FIG. 1) may provide air to the air duct 118. In one exemplary implementation, the damper is charged or pressurized to 25-30 inches water column (62-75 mBar). In response to the pulse of air, the agitator 108 rapidly floats to the surface of the pond 100 and emerges there. The movement of the agitator 108 through the vertical distance 120 creates a propagating wave 112. The agitator 108 is allowed to deflate and re-submerge into pond 100 to await another inflation cycle. In a preferred implementation, several inflations are performed per minute. Accordingly, several propagating waves 112 may be incident in the pond 100 at any given time depending on the dimensions of the pond 100 and other conditions.

In an example of such implementation, a 12-inch (30 cm) diameter bladder or agitator 108 at rest is deflated such that about 24 inches (61 cm) of its diameter is deflated or collapsed. The result is about a 12-inch (30 cm) diameter partially or fully submerged agitator 108, or about a six-inch (15 cm) diameter partially or fully submerged agitator 108. When pulsed with air, the bladder or agitator 108 is again inflated and displaces about 0.75 cubic feet ($ft^3$) of water for each running foot of agitator corresponding to about 0.07 cubic meters of water for each meter of agitator. After causing a pulse or relatively rapid inflation, another fast acting damper (not shown) is used to deflate the agitator 108. In addition to (or in place of) a deflating damper, deflation vents or vent holes may installed in the agitator 108 or inflatable portion of the agitator 108. In one implementation, one or more deflation vents are located along a bottom edge of the agitator 108 so as to encourage draining of any water that enters the agitator 108. Even with some water entering the agitator 108, inflation and deflation of the agitator 108 causes substantial and sufficient agitation so as to create a propagating wave that travels all or substantially all of the length or width 114 of the pond 100.

Alternatively, other movements and other means may be used to cause a propagating wave 112. For example, the agitator 108 may remain inflated and may be rapidly moved downward or pulsed rapidly in a horizontal or other direction(s) (not shown) to cause the propagating wave 112. In yet another alternative example, instead of using air to inflate the agitator 108, a series of cables or cords are used to provide a pulsing motion to the buoyant agitator 108. In yet another alternative, the agitator 108 is made of two or more materials such as one or more foam portions and one or more hollow or inflatable portions. An air pump would then only need to fill or partially fill a smaller volume to cause the agitator 108 to float to the surface of the pond 100. In any event, the agitator 108 may be made of other materials (e.g., wood, straw, composite, dried and treated algae, metal, foam polymer).

With reference to FIG. 1, algae cultivation preferably includes a nutrient line 122 at or near the distal edge 116 of the pond 100. The nutrient line 122 preferably runs along substantially all or a substantial part of the length or side 124 of the pond 100. In a preferred implementation, the length 124 of the pond 100 is substantially larger than the width 114 of the pond 100. Nutrients (not shown) are released into the medium 102 over the course of time. Nutrients may be intermittently supplied, or may be continuously fed to the medium 102. Nutrients or a nutrient-enriched flow is provided to the nutrient line 122 through a nutrient supply 126. The nutrient line 122 may require an intake line (not shown) that draws medium 102 from the pond 100 and recycles it to the pond 100. A nutrient line 122 alternatively may deliver a variety of materials not traditionally considered as "nutrients" or fertilizers for algae including carbon dioxide or other off gases from power plants, or other gaseous or liquid based materials from production or processing facilities. By delivering materials to algae ponds, materials can be sequestered or captured by algae or other organism cultivated in ponds. While a single nutrient line 122 is shown, multiple nutrient lines may be provided. One or more nutrient lines may be arranged in or around the pond 100 in a variety of ways conforming to the needs of the algae, environment and pond 100.

Figure 2:
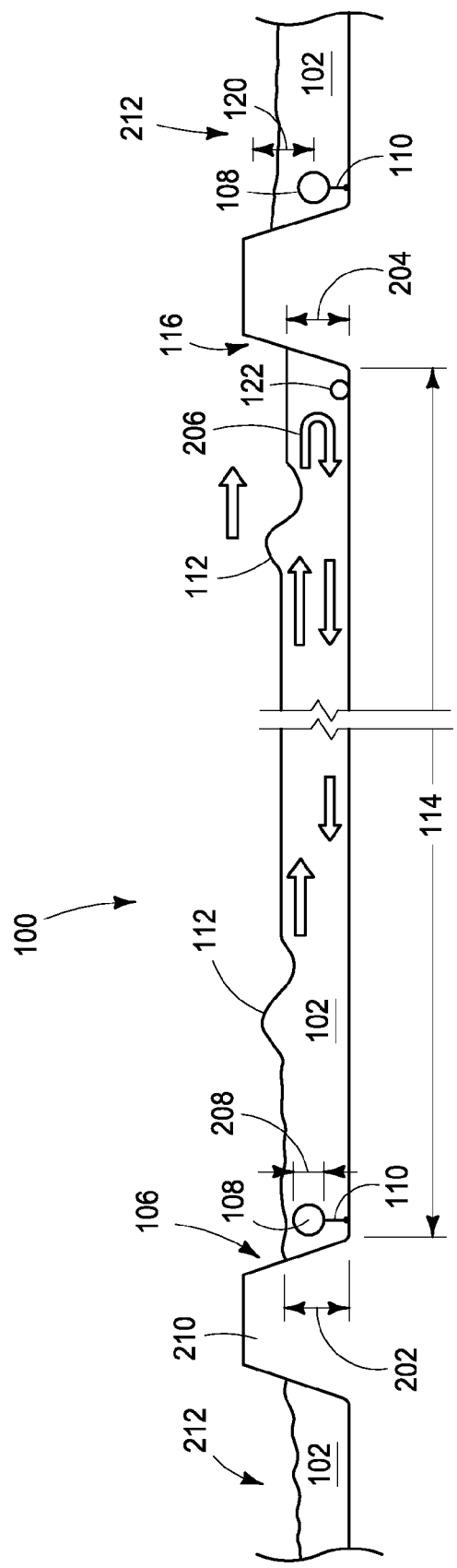
FIG. 2 shows a profile cross-sectional view of an algae cultivation pond and exemplary agitation mechanism according to one implementation of the invention.

FIG. 2 shows a profile or lateral cross-sectional view of an algae cultivation pond 100 and exemplary agitation mechanism according to one implementation of the invention. The elements shown in this view are not drawn to scale but are shown for illustration purposes only. (The same applies to the other figures.) The width 114 and pond 100 are cut to show that the width 114 and pond 100 are not limited in size relative to the length (not shown) of the pond 100 or consistent with other typical algae ponds. With reference to FIG. 2, an agitator 108 is located at the proximal edge 106 of the pond 100 such as by one or more anchors 110. The proximal depth 202 of the pond 100 (or, more accurately, the depth of the medium 102 near the proximal end 106) as measured at or near the proximal edge 106 is preferably larger or deeper than a distal depth 204. However, the proximal depth 202 and the distal depth 204 may be the same or about the same. As a specific example, a proximal depth 202 could be about 20 inches (51 cm) and a distal depth 204 could be about 12 inches (30 cm). In this example, for a round-shaped agitator 108, a diameter 208 of the agitator 108 could be about 12 inches (30 cm).

Propagating waves 112 originate at and travel from the proximal edge 106 to or toward the distal edge 116. In one example, propagating waves are generated by a generally rapid and generally vertical movement of the agitator 108 shown by a distance 120 in FIG. 2. As viewed along the width 114 of the pond 100, the bottom of the pond 100 is preferably substantially smooth to encourage recycle 206 of flow of medium 102 and nutrients (not shown) from the area near the nutrient line 122. In one implementation, leveling machinery is used to create a substantially smooth pond bottom that has little or no slope. In another implementation, a slight slope is provided to each pond with a proximal depth 202 being greater than a distal depth 204. Nutrients may be carried from the distal end 116 toward the proximal 106 in a countercurrent fashion in the pond 100 as shown by the arrows in FIG. 2. Thus, nutrients may travel by diffusion and circulation of the medium 102.

The propagating waves 112 are useful for more than dispersing nutrients. First, the propagating waves 112 agitate the surface of the medium 102. Such agitation encourages exchange of oxygen, nitrogen and carbon dioxide with the ambient air. Carbon dioxide is generally absorbed by the algae and oxygen is released into the medium 102 and ultimately the ambient air. Second, the propagating waves 112 agitate the medium 102. As algae captures light at the surface of the pond 100, the algae grows. The agitation of the medium circulates growing algae to other depths of the medium 102 thereby allowing the algae to grow to a greater depth than would normally grow without agitation, which, in turn, causes increased growth of biomass over a same amount of time as compared to a stagnant pond or one that is agitated with impellers or propellers. Third, the propagating waves 112 promote dispersion of nutrients along the width 114 of the pond 100. Without propagating waves 112, nutrients generally have to be introduced at a substantially greater number of locations in each pond 100 or in a more cumbersome fashion. A first pond 100 is separated from neighboring ponds 212 by berms 210. The width of each berm 210 may be selected based on convenience when harvesting algae from a series of neighboring ponds 100 and 212, or the width of each berm 210 may be uniform.

Alternatives

Figure 3:
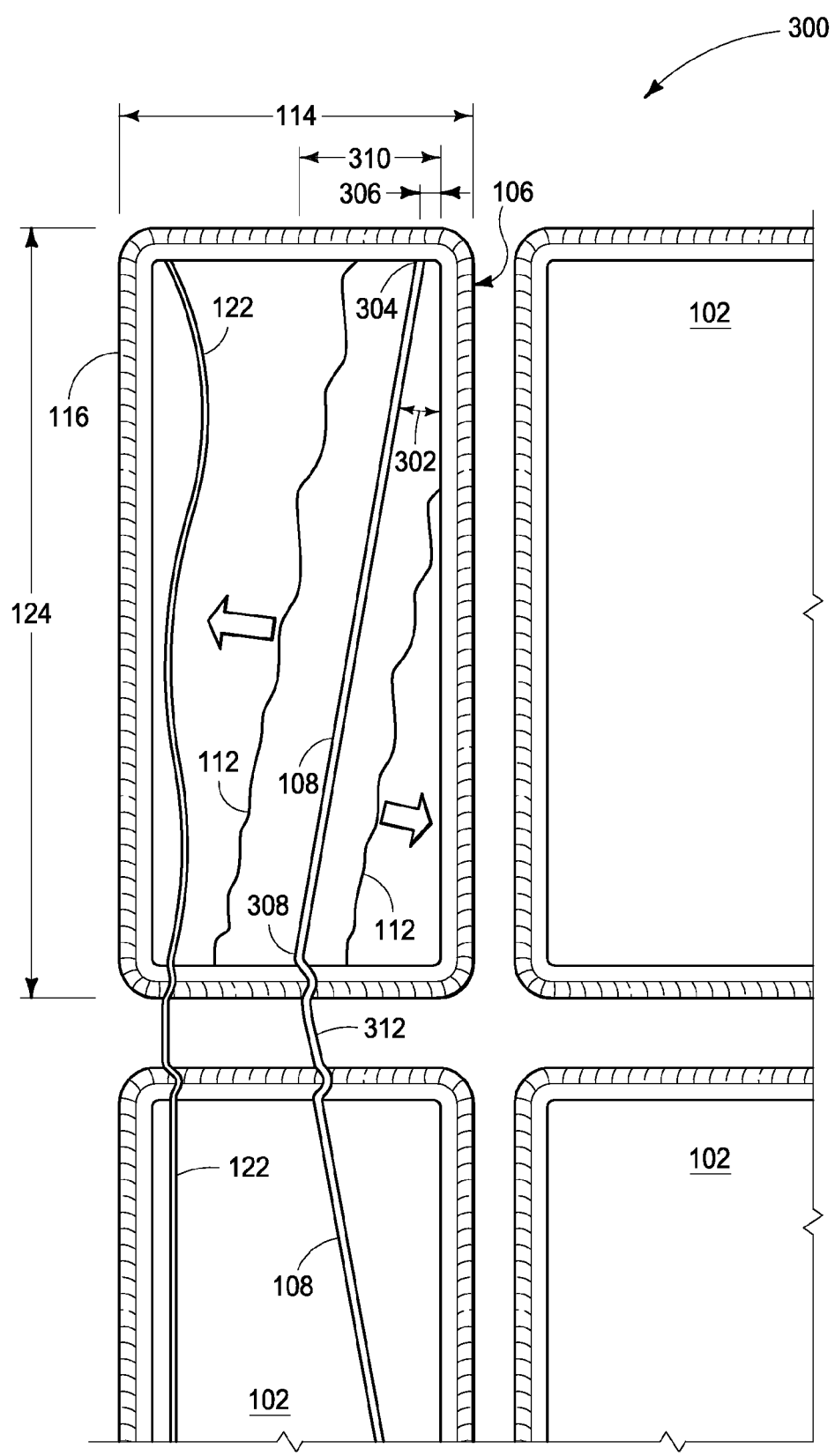
FIG. 3 shows an overhead view of an algae cultivation pond and exemplary agitation mechanism according to an alternative implementation of the invention.

FIG. 3 shows an overhead view of an algae cultivation pond and exemplary agitation mechanism according to an alternative implementation 300 of the invention. With reference to FIG. 3, an agitator 108 is placed at an arbitrary distance along the width 114 of the pond; in FIG. 3, the agitator 108 is shown located somewhat toward the proximal edge 106 of the pond. The agitator 108 is placed at an arbitrary angle 302 as measured between a line parallel with the proximal side 106 of the pond and the agitator 108. A first end 304 of the agitator 108 is located a first distance 306 from the proximal edge 106 of the pond. A second end 308 of the agitator 108 is located a second distance 310 from the proximal edge 106 of the pond. In this example, propagating waves 112 are directed to both the proximal edge 106 and the distal edge 116 of the pond. The alternative arrangement may reduce the amount of equipment needed to supply propagating waves 112 to the pond, or may reduce the number of ponds (not the surface area of cultivation or volume of media 102) needed to cultivate a desired amount of algae. This alternative arrangement may allow the ponds to be of other than rectangular shape, or may allow for increased propagation of waves or some other benefit. The alternative arrangement may provide needed flexibility based on construction, harvesting or other considerations or restrictions.

In an alternative implementation, the agitator 108 may occupy substantially all of the length 124 of the pond 100 as shown in FIGS. 1, 3. In another implementation, the agitator 108 merely occupies a portion of the length 124 of the pond. In yet other implementation, the agitator 108 is broken into several portions or units (not shown in FIGS. 1, 3). Each agitator unit may operate independently of other agitator unit(s), or may act in concert or coordination with other agitator unit(s). For example, each unit may operate in sequence to cause a rolling wave or wave that travels in a direction that is not substantially parallel to the width 114 or length 124 of the pond 100. Alternatively, the units may operate in sequence starting at a middle portion of the length 124 of the pond 100 and ending at the edges of the pond—a V-shaped wave may be created and propagated.

In yet another alternative implementation, waves of different magnitudes may be generated over time. For example, propagating waves 112 may be created in a pattern or rhythm such as two waves of relatively small magnitude followed by two waves of relatively large magnitude. In this example, perhaps the waves of relatively small magnitude fail to reach the distal edge 116 of the pond 100, but the waves of relatively large magnitude do so. In yet another variation of propagating waves 112, as the algae biomass increases over time, the magnitude of propagating waves 112 is increased as needed or as measured (e.g., in real time) to ensure that the propagating waves 112 reach the distal end 116 of the pond 100 or detectably reach a point of measurement along the length 114 of the pond 100. In such a scenario, a propagating wave magnitude sensor (not shown) relays feedback to the control system of the actuator of the agitator 108 so that a proper or desired magnitude of propagating wave 112 is delivered at any given time. Propagating waves 112 may be varied in frequency depending on a variety of factors including, but not limited to, time of day, day versus night, width of the pond, density of algae, strain or type of algae, depth of water in the pond, age of the inflatable agitator.

In the implementation shown in FIG. 3, a bridging section 312 may connect agitators 108 in neighboring ponds. That is, compressed air may be passed into the agitators 108 of neighboring ponds at substantially the same time, or that agitators 108 of neighboring ponds may be actuated at substantially the same time or through the same actuation or mechanism.

Scaling Up

Figure 4:
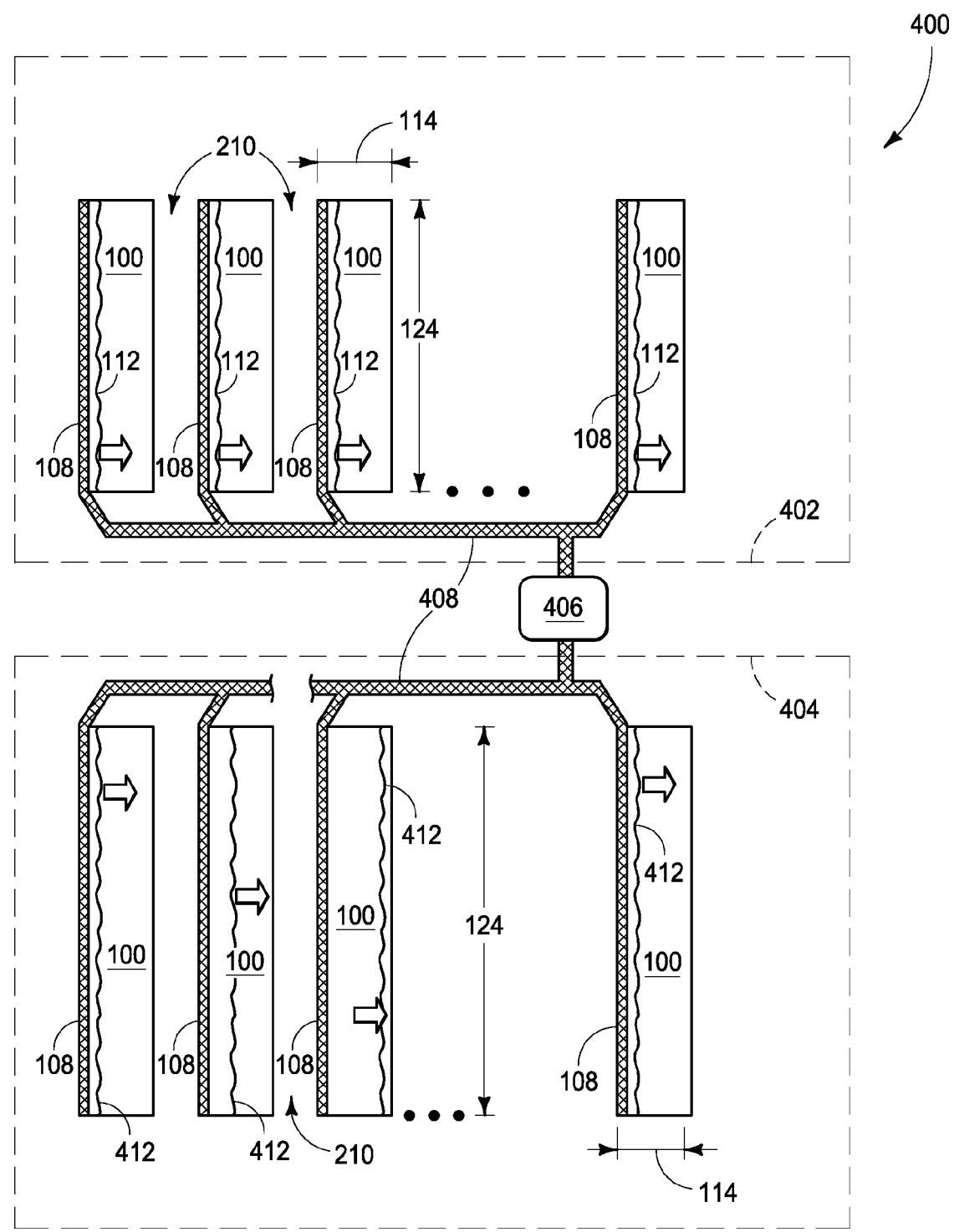
FIG. 4 shows an overhead view of an array of algae cultivation ponds and system of agitation mechanisms for production of algae on an industrial scale according to one implementation of the invention.

FIG. 4 shows an overhead view 400 of an algae cultivation system including a set of algae cultivation ponds and a system of agitation mechanism(s) for production of algae on an industrial scale according to one implementation of the invention. With reference to FIG. 4, a first array 402 and a second array 404 of cultivation ponds 100 are evident. As one example of the arrangement of ponds, each of the ponds may be about 40 feet (12 meters) in width 114. Given that each pond 100 is about 1 mile long (1.6 km), about 120 ponds may be placed side by side in a square mile with about 4 feet (1 meter) of berm 210 between neighboring ponds 100. During algae cultivation, propagating waves 112 are capable of traveling from one edge of these mile-long ponds to the other. Other arrangements are possible. For example, ponds 100 may be about ¼ mile (0.4 km) long. One disadvantage of such an arrangement would be the requirement for four times the number of agitators 108 and increased amount equipment needed to actuate the agitators 108.

An industrial scale compressor 406 provides air through ducts 408 to agitators 108. Control equipment such as valves, computers, actuators and the like are not shown in FIG. 4. However, it is to be understood that such are used to operate the agitators 108 and other components of the system. For example, dampers (not shown) provide pulses of air to agitators 108.

In a first array or set of ponds 402, the agitators 108 are operated in synchronization with each other. This is evident by the propagating waves 112 shown at about the same position in each of the ponds 100 at a given instant of time. In this implementation, air is introduced into each inflatable portion of the agitators 108 at about the same time. This may be accomplished by connecting neighboring agitators 108 with each other so that only one or just a few ducts 408 are needed to actuate agitators in the ponds 100 in the first array 402.

In another implementation, in the second array 404 of ponds, the agitators 108 are operated (one or more at a time) in series according to a control scheme. For example, each of the agitators 108 receives a pulse of air from the compressor 406 in turn. This is evident by the propagating waves 412 shown at different positions in each of the ponds 100 at the given instant of time. This scheme would require a damper for each agitator or group of agitators 108 receiving a pulse of air. The scheme in the second array 404 provides a more balanced load on the compressor 406 and related equipment.

The air compressor 406, ducts 408 and various equipment could be sized depending on a variety of factors including (but not limited to): the number of propagating waves desired each hour for each pond, the desired size of propagating wave in each pond, the length or width of each pond or the array of ponds, the number of agitators operating in tandem or synchronization, the ambient temperature, the amount of algae biomass in each pond, and the energy source used to compress the air. In one implementation, an air compressor 406 is sized to supply enough compressed air for operating agitators 108 in both the first array 402 and second array 404.

In one implementation, an algae cultivation and harvesting system comprises a central facility for growth media preparation, one or more feed canals a set of pulse agitated cultivation ponds 402 and one or more harvest canals.

The growth media for the algae may be enriched with carbon dioxide. There are many sources of carbon dioxide. A predominant source of the carbon dioxide may be a gaseous exhaust of an industrial scale fermentation, industrial combustion gaseous exhaust, or may be taken from a source of geologically-derived carbon dioxide, or any combination of such sources such as a combination of gaseous exhaust of an industrial scale fermentation, geological carbon dioxide, and gaseous exhaust from an industrial combustion.

The algae cultivation system shown in FIG. 4 preferably includes pulsed agitation predominantly across the respective short dimension of each pond 100. During cultivation, it may become necessary to include a source of makeup water. This makeup water may be derived from various sources including from: oil and gas production water, saline aquifers, inland saline lakes, sea water, surface fresh water, and fresh water aquifers.

The algae cultivation system such as the one shown in FIG. 4 may produce a wet algal cake or a dry algal powder. The algae cultivation system or facility may an algal product into two or more commodities. Alternatively, the cultivation facility may use fermentation to separate starch and sugar from protein, oils, or from the protein and oils. The ponds 100 of the algae cultivation system may be covered, lined, or covered and lined. The pulse agitation sub-system 406, 408 (and other parts not shown in FIG. 4) may include a source of compressed air, ducts to distribute the compressed air, and control dampers. The in-pond agitators may take the form of ballasted floating bladders.

Figure 5:
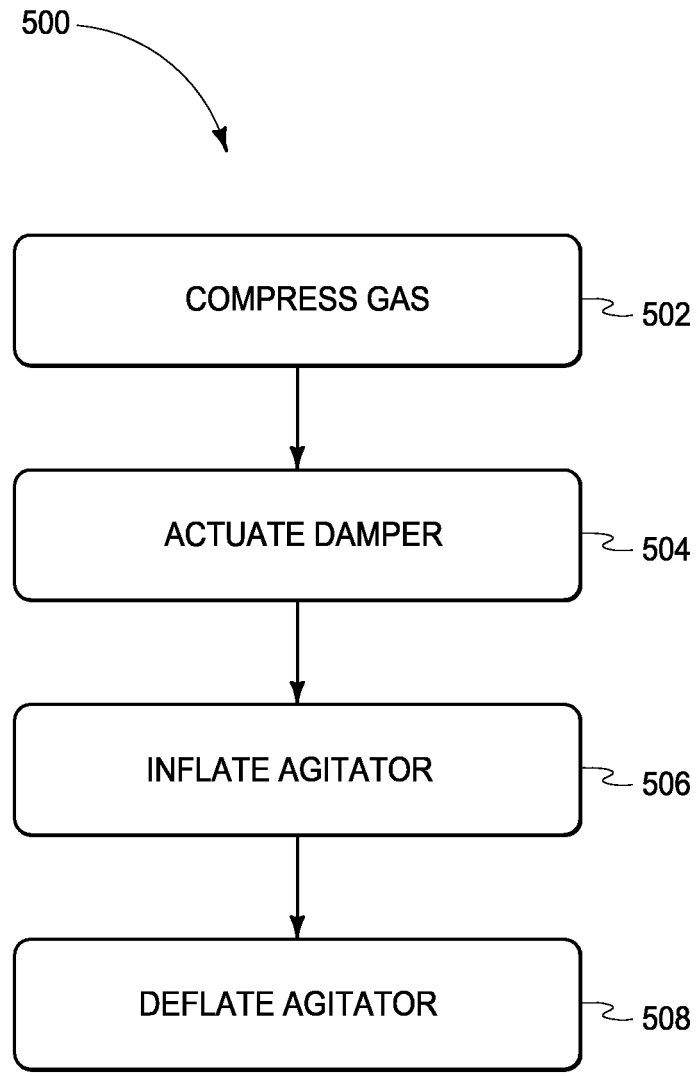
FIG. 5 shows a flowchart of one implementation of a method for causing agitation (e.g., propagating wave) in an algae cultivation pond.

FIG. 5 shows a flowchart 500 of one implementation of a method for causing agitation (e.g., propagating wave) in an algae cultivation pond. With reference to FIG. 5 and as explained at least in reference to FIG. 4, a compressor may compress air or other gas 502. When desired, a damper is actuated 504 and an inflatable portion or portions of an agitator are inflated 506. The action of pulsing or relatively rapidly inflating the agitator 506 causes a propagating wave in the growth medium of an algae pond. The propagating wave travels in the algae pond. Before a next pulsing, the agitator is deflated 508. Deflation allows the agitator to sink back into the pond or otherwise configure itself to a starting or ready position. It is through intermittent or cyclical application of pulses of compressed air or gas that propagating waves are introduced into a pond and thereby improves or encourages growth of algae.

Figure 6:
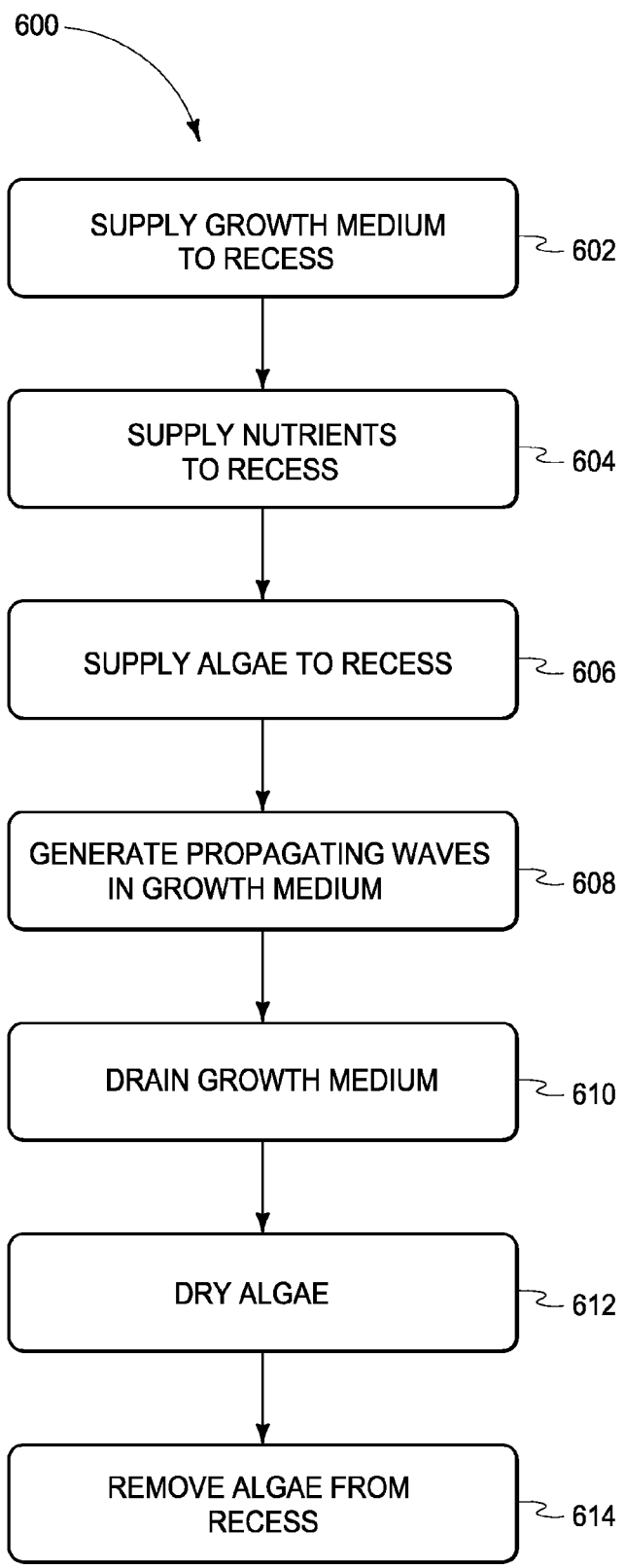
FIG. 6 shows a flowchart of one implementation of a method for cultivating algae according to the invention.

FIG. 6 shows a flowchart of one implementation of a method for cultivating algae according to the invention. With reference to FIG. 6, algae may be cultivated by supplying growth medium to a recess 602. The recess may or may not be lined or enclosed. Generally, a recess is a pool, pond, furrow, channel, tube or canal formed specifically for the purpose of cultivating algae. Nutrients and other materials may be supplied to the growth medium 604, either before, during or after algae is supplied to the growth medium and recess 606. These first steps 602, 604 and 606) may be performed in any order, all at once, intermittently, or continuously. At some point in time, propagating waves are generated in the growth medium 608. The propagating waves may be generated frequently or infrequently, but at least frequently enough to provide improved growing conditions over those associated with a non-agitated growth medium.

When it is time for algae harvesting, the growth medium in the recess is drained 610, and the algae is dried or allowed to dry 612. In preparation for another batch of algae, the dried or partially dried algae is removed from the recess 614. The process or method for cultivating algae may then be repeated.

Glossary

Unless stated otherwise, or found in conflict, the following language provides at least one meaning of the terms used herein to describe and explain the invention.

Algae medium refers to the liquid, fluid, water and the like refer to the liquid medium resident in ponds for algae or biomass cultivation. An example of an algae medium is found in FIG. 1 as 102.

An algae cultivation pond or reservoir has been referred herein to an open recess in which a liquid medium for algae or biomass cultivation is disposed. However, the concepts described apply equally well to all sizes, shapes and arrangements of equipment and materials. For example, propagating waves may be applied from a nano-scale up to and including ponds and reservoirs that are miles in length.

Although the present invention has been described with reference to specific exemplary embodiments, it will be evident that the various modification and changes can be made to these embodiments without departing from the broader spirit of the invention. In an area of technology such as this, where growth is fast and further advancements are not easily foreseen, the disclosed embodiments may be readily modifiable in arrangement and detail as facilitated by enabling technological advancements without departing from the principals of the present disclosure.

I claim:

1. A system for cultivating algae, the system comprising:
    a recess in a portion of earth, and wherein the recess is at least partially filed with an aqueous growth medium that is capable of sustaining algae growth, and wherein the recess includes a proximal side, a distal side, a width, a length and a bottom surface, and wherein the bottom surface is sloped such that a depth of the aqueous growth medium at the proximal side of the recess is greater than a depth of the aqueous growth medium at the distal side of the recess;
    a movable and floatable agitator having a length that is substantially the length of the recess, and wherein the agitator further includes an inflatable portion and deflation vents located along the length of the agitator and located along a bottom of the inflatable portion, and wherein the deflation vents are configured to allow aqueous growth medium to escape the inflatable portion of the agitator when the inflatable portion is exposed to compressed gas and configured to allow aqueous growth medium to enter the inflatable portion when compressed gas is not being pulsed into the inflatable portion, and wherein the agitator is placed in the aqueous growth medium near the proximal side in the recess, and wherein the agitator is movable relative to a surface of the recess, and
    wherein the agitator is in a partially deflated and at least a partially submerged state at a first position in the recess during a first portion of a movement cycle, and
    wherein the agitator is capable of intermittently causing a propagating wave in the aqueous growth medium when the inflatable portion receives a pulse of compressed gas, and
    wherein the agitator is configured to advance the propagating wave from a region proximate to the agitator to the distal side of the recess during each movement cycle of the agitator;
    an actuator in fluid connection with the agitator, and
    wherein the actuator includes a damper and a controller which controls operation of the damper, and
    wherein the actuator is configured with instructions to pulse compressed gas into the inflatable portion of the agitator during the first portion of the movement cycle by manipulation of the damper, and wherein the pulsed gas causes the agitator to at least partially float to a second position and move relative to the first position in the aqueous growth medium, and wherein the actuator is configured to cease flow of compressed gas into the inflatable portion during a second portion of the movement cycle and thereby allow aqueous growth medium to re-enter the inflatable portion via the deflation vents and allow the agitator to return to the first position in the recess, and
    wherein activation of the actuator causes drainage of aqueous growth medium from the agitator and causes temporary floatation of the agitator and thereby generates a propagating wave in the aqueous growth medium of the recess; and
    a source of compressed gas in fluid connection with the agitator via the actuator.

2. The system for cultivating algae of claim 1, wherein the inflatable portion of the movable and floatable agitator includes a valve in fluid communication with the inflatable portion of the agitator and that is capable of controlling release of gas from the inflatable portion of the agitator, and wherein the controller operates the valve in synchronization with the damper so that the valve opens after closing of the damper and the pulsing of gas into the inflatable portion of the agitator.

3. The system of claim 1, and wherein the inflatable portion is a cylindrical bladder that is approximately at least 10 inches (25 cm) in diameter and that displaces at least 0.5 cubic feet (14.1 L) of aqueous growth medium for each linear foot (30.5 cm) of cylindrical bladder.

4. The system of claim 1, and wherein the movable and floatable agitator includes anchors fixed to the agitator at one end of each anchor and to the recess at the other end of each anchor, and wherein the anchors cause the movable and floatable agitator to remain at the first position until compressed gas is pulsed into the agitator.

5. The system of claim 1, and wherein the movable and floatable agitator is made from a flexible plastic material, and wherein the second position is substantially in a vertical direction relative to the first position.

6. The system of claim 1, and wherein the system further comprises a liner placed along a surface of the recess, and wherein the pulsed air is pressurized to at least 60 mBar of pressure prior to being pulsed into the inflatable portion of the agitator.

7. The system of claim 1, and wherein the depth along the proximal side is substantially uniform, and wherein the depth along the distal side is substantially uniform.

8. The system of claim 1, and wherein the bottom surface is substantially smooth over a substantial portion of the recess.

9. The system of claim 1, and wherein a first end of the agitator is placed a first distance from the proximal side of the recess and a second end of the agitator is placed a second distance from the proximal side of the recess, and wherein the first distance and second distance are different from one another, and wherein the propagating wave is a first propagating wave and the first propagating wave is directed to the distal side of the recess, and a second propagating wave is substantially simultaneously directed toward the proximal side of the recess.

10. The system of claim 1, and wherein the system further comprises:
- a sensor in communication with the controller, and wherein the sensor is placed at a point proximate to a distal side of the recess to provide to the controller a real-time signal representative of a magnitude of a propagating wave reaching the sensor, and wherein the controller is programmed with instructions to cause the actuator to generate propagating waves of an increased magnitude based on the real-time signal from the sensor so as to ensure a detectable propagating wave reaches the sensor.

11. The system of claim 1, and wherein the system further comprises a light sensor in communication with the controller, and wherein the controller is programmed with instructions to operate the actuator at a first frequency during detection of a threshold amount of light by the light sensor and programmed with instructions to operate the actuator at a second frequency otherwise.

12. The system of claim 1, and wherein the recess is a first recess, and wherein the movable and floatable agitator is a first agitator, and wherein the system further comprises:
- a second recess at least partially filed with an aqueous growth medium that is capable of sustaining algae growth, and wherein the second recess is separated from the first recess by a berm;
- a second movable and floatable agitator placed in the aqueous growth medium in the second recess, and wherein the actuator is also in connection with the second agitator, and wherein the second agitator is movable relative to a surface of the second recess, and wherein the second agitator includes an inflatable portion, and wherein the second agitator is in at least a partially deflated state at a first position during an initial portion of a movement cycle, and wherein the second agitator is independently controllable from the first agitator, and wherein the second agitator is capable of intermittently causing a propagating wave in the aqueous growth medium, and wherein the second agitator is configured to advance the propagating wave from a region proximate to the second agitator to the distal side of the second recess during each movement cycle of the second agitator; and
- wherein the controller is programmed with instructions to operate the actuator to cause operation of the first agitator out of synchronization with operation of the second agitator so as to reduce a load on the actuator during agitation of the first recess and the second recess.

13. The system of claim 1, and wherein the movable and floatable agitator lies contiguous to a bank of the recess at a border of the aqueous medium when the agitator is in the partially submerged state at the first position.

14. The system of claim 1, wherein the inflatable portion of the agitator is in excess of the width of the recess, and wherein the length of the recess is at least 1,000 feet, and wherein the width of the recess is less than 40 feet, and wherein the agitator is placed along the width of the recess, and wherein propagating waves travel along the length of the recess.

15. The system of claim 1, wherein the agitator further includes a floatable foam portion positioned inside the inflatable portion of the agitator so as to reduce an amount of pulsed compressed gas required to at least partially float the agitator, and wherein the floatable foam portion is insufficient to cause the agitator to initiate a floating motion without introduction of pulsed gas into the inflatable portion of the agitator.

* * * * *